(12) United States Patent
Eil

(10) Patent No.: US 11,307,658 B2
(45) Date of Patent: *Apr. 19, 2022

(54) BINOCULAR SYSTEM FOR ENTERING COMMANDS

(71) Applicant: ALCON INC., Fribourg (CH)

(72) Inventor: Martin Eil, Berlin (DE)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/951,856

(22) Filed: Nov. 18, 2020

(65) Prior Publication Data

US 2021/0072826 A1    Mar. 11, 2021

Related U.S. Application Data

(63) Continuation of application No. 16/444,561, filed on Jun. 18, 2019, now Pat. No. 10,871,824.

(60) Provisional application No. 62/690,204, filed on Jun. 26, 2018.

(51) Int. Cl.
  *G09G 5/00* (2006.01)
  *G06F 3/01* (2006.01)
  *G02B 23/10* (2006.01)
  *G06F 3/0482* (2013.01)

(52) U.S. Cl.
  CPC ............. *G06F 3/013* (2013.01); *G02B 23/10* (2013.01); *G06F 3/0482* (2013.01)

(58) Field of Classification Search
  CPC ...... A61B 3/113; G02B 21/20; G02B 21/368; G02B 23/10; G02B 25/001; G02B 27/0093; G02B 27/106; G02B 27/145; G06F 3/011; G06F 3/013; G06F 3/0482
  See application file for complete search history.

(56) References Cited

U.S. PATENT DOCUMENTS

| | | | |
|---|---|---|---|
| 2002/0113943 A1* | 8/2002 | Trajkovic | G02B 27/0093 351/209 |
| 2015/0049013 A1* | 2/2015 | Rahman | G06F 3/011 345/156 |

* cited by examiner

*Primary Examiner* — Insa Sadio

(57) ABSTRACT

In certain embodiments, a binocular system for entering commands includes a computer and a binocular eyepiece. The computer generates a virtual graphical user interface (GUI) with one or more graphical elements, where each graphical element corresponds to a command. The binocular eyepiece includes of eyepieces. Each eyepiece has an optical path that directs an image of an object towards a corresponding eye of a pair of eyes. The optical path of at least one eyepiece directs the virtual GUI towards the corresponding eye. At least one eyepiece is associated with an eyetracker that tracks movement of the corresponding eye relative to the virtual GUI to yield a tracked eye. The computer interprets movement of the tracked eye relative to the virtual GUI as an interaction with a selected graphical element, and initiates the command corresponding to the selected graphical element.

16 Claims, 4 Drawing Sheets

BINOCULAR SYSTEM FOR ENTERING COMMANDS

CROSS-REFERENCE TO RELATED APPLICATIONS

This application is a continuation of U.S. application Ser. No. 16/444,561, filed Jun. 18, 2019, which claims the benefit of U.S. Provisional Application No. 62/696,204, filed Jun. 26, 2018, the entire contents of which are incorporated herein by reference.

TECHNICAL FIELD

The present disclosure relates generally to controlling medical systems, and more specifically to a binocular system for entering commands.

BACKGROUND

Medical devices can perform a wide variety of actions in response to commands from an operator. For example, an operator can select commands from a command panel to change magnification, focus, and brightness of a microscope. Entering commands for a medical device, however, has special concerns. Touching the command panel can contaminate the panel. Moreover, searching for the part of the panel to enter the command takes time and attention away from the user. Accordingly, known command panels are sometimes not suitable for certain situations.

BRIEF SUMMARY

In certain embodiments, a binocular system for entering commands includes a computer and a binocular eyepiece. The computer generates a virtual graphical user interface (GUI) with one or more graphical elements, where each graphical element corresponds to a command. The binocular eyepiece includes of eyepieces. Each eyepiece has an optical path that directs an image of an object towards a corresponding eye of a pair of eyes. The optical path of at least one eyepiece directs the virtual GUI towards the corresponding eye. At least one eyepiece is associated with an eye-tracker that tracks movement of the corresponding eye relative to the virtual GUI to yield a tracked eye. The computer interprets movement of the tracked eye relative to the virtual GUI as an interaction with a selected graphical element, and initiates the command corresponding to the selected graphical element.

In certain embodiments, a method for entering commands using a binocular system includes generating, by a computer, a virtual graphical user interface (GUI) comprising one or more graphical elements. Each graphical element corresponds to a command. An optical path of each eyepiece of a binocular eyepiece directs an image of an object towards a corresponding eye of a pair of eyes. The optical path of at least one eyepiece directs the virtual GUI towards the corresponding eye. An eye-tracker associated with at least one eyepiece tracks movement of the corresponding eye relative to the virtual GUI to yield a tracked eye. A movement of the tracked eye relative to the virtual GUI is interpreted as an interaction with a selected graphical element. The command corresponding to the selected graphical element is initiated.

BRIEF DESCRIPTION OF THE DRAWINGS

Embodiments of the present disclosure are described by way of example in greater detail with reference to the attached figures, in which.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
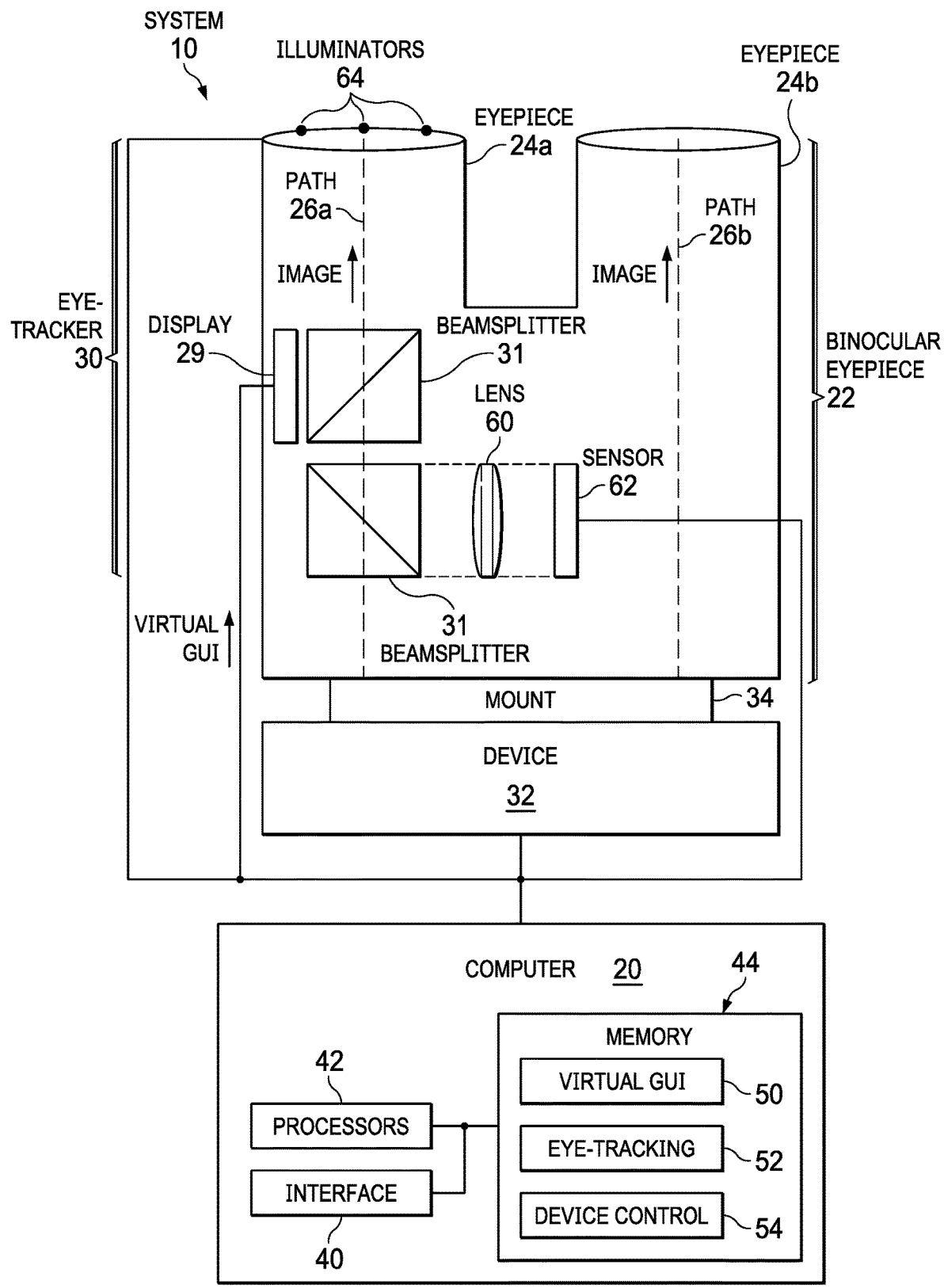
FIG. 1 illustrates one embodiment of a binocular system that allows a user to enter commands with eye movements.
Figure 2:
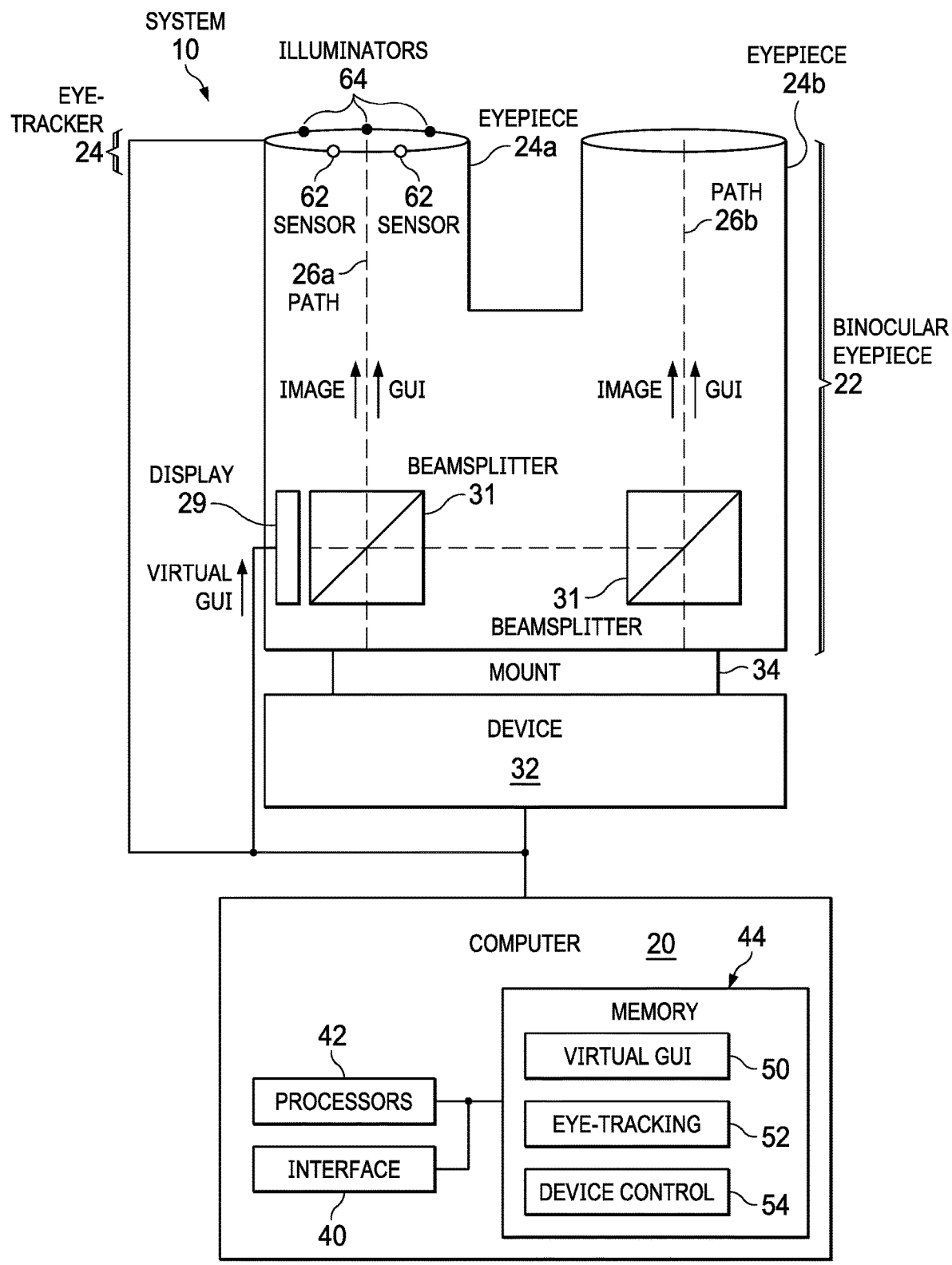
FIG. 2 illustrates another embodiment of a binocular system that allows a user to enter commands with eye movements.

FIGS. 1 and 2 illustrate embodiments of a binocular system 10 that allows a user to enter commands with eye movements. The illustrated examples, system 10 includes a computer 20 and a binocular eyepiece 22 coupled to a device 32 with a mount 34. Computer 20 includes an interface 40, one or more processors 42, and one or more memories 44, which stores logic such as computer programs for virtual GUI 50, eye-tracking 52, and device control 54. Binocular eyepiece 22 includes eyepieces 24, a display 29, an eye-tracker 30, and one or more beamsplitters 31. Eye-tracker 30 includes a lens 60, a sensor 62, and illuminators 64.

In an example of operation, binocular system 10 allows a user to enter commands to any suitable device 32, such as a medical device. Computer 20 generates a virtual graphical user interface (GUI), which is an image comprising graphical elements corresponding to commands. Eyepieces 24 each have an optical path 26 that directs an image of an object towards a corresponding eye of a pair of eyes. An optical path 26 of one or both eyepieces 24 also directs the virtual GUI towards the corresponding eye. One or both eyepieces 24 is associated with an eye-tracker 30 that tracks movement of the corresponding eye relative to the virtual GUI. Computer 20 interprets a movement of the tracked eye relative to the virtual GUI as an interaction with a selected graphical element, and initiates the command corresponding to the selected graphical element.

In certain embodiments, computer 20 generates a virtual GUI, which is delivered along an optical path 26 to at least one eye. The virtual GUI includes one or more graphical elements, which may have any suitable size or shape. Each graphical element corresponds to a command, or instruction, to device 32, typically to perform an action, e.g., accept a selection or setting defined by the user, perform a user-selected operation programmed into computer 20, display information requested by the user, or other suitable action. A user may enter a command by making his/her gaze interact with the graphical element corresponding to the command in a manner that signals selection of the element. An interaction is a movement of the eye (e.g., moving or directing eye gaze or blinking the eye) relative to a graphical element that indicates, e.g., selection of the element. For example, the user may direct his/her gaze at the element for at least a predefined amount of time, e.g., at least 3, 5, or 10 seconds. As another example, the user may direct his/her gaze at the element and may blink a predetermined amount of times, e.g., 1, 2, or 3 times. In certain embodiments, the interaction may be confirmed by movement of another part of the user's body. For example, the user may direct his/her gaze towards an element to select the element, and then confirm selection of the element by, e.g., stepping on a foot pedal with his/her foot or pressing a physical button with his/her hand. In certain embodiments, the virtual GUI can indicate if a user's gaze has interacted with or selected an element. For example, the virtual GUI can highlight (e.g., make brighter or change color of) an element that the user's gaze has selected. The user may confirm selection by, e.g., blinking or moving a hand or foot. Examples of virtual GUIs are described in more detail with reference to FIGS. 3A and 3B.

Eyepieces 24 (24a,b) of binocular eyepiece 22 correspond to a pair of eyes. Generally, one eyepiece 24a corresponds to one eye, e.g., the left eye, and another eyepiece 24b corresponds to the other eye, e.g., the right eye. An eyepiece 24 may be a generally tubular shaped housing with one or more optics that defines an optical path 26 (i.e., the path that light can travel) through eyepiece 24. An optic may be, e.g., a lens, splitter, prism, coated glass, or mirror, or a system that include multiple optics, such as a lens system. Paths 26 (26a,b) of eyepieces 24 (24a,b) generally directs an image of an object towards a corresponding eye of a pair of eyes. For example, device 32 may be a microscope that captures an image of an object, and paths 26 may direct the image of the object towards the eyes.

Path 26 of one or both eyepieces 24 may receive the virtual GUI from computer 20 and direct the GUI towards the corresponding eye. In FIG. 1, path 26a of eyepiece 24a directs the GUI, and in FIG. 2, paths 26a,b of eyepieces 24a,b directs the GUI. Virtual GUI program 50 of computer 20 generates image data that describes virtual GUI. The image data is sent to display 29, which displays the GUI. Any suitable display may be used, e.g., a display that uses light-emitting diode (LED), micro-organic light-emitting diode (micro-OLED), liquid-crystal display (LCD), digital light processing (DLP), liquid crystal on silicon (LCoS), or LED beamer technology. Display 29 may have any suitable size and shape, and may be in any suitable location. In FIG. 1, display 29 is proximate a beamsplitter 31 that receives and reflects the virtual GUI and the image of the object and directs them along path 26. In FIG. 2, display 29 is proximate beamsplitters 31 that receive and reflect the virtual GUI and the image of the object and directs them along paths 26. In other embodiments, display 29 may be located towards the end of eyepiece 24 proximate to an eye, and the eye can view the virtual GUI directly from display 29.

At least one eyepiece 24 is associated with an eye-tracker 30 that tracks movement of an eye relative to the virtual GUI, indicating the area of the GUI where the gaze is directed, i.e., where the eye is looking. An eyepiece 24 that is "associated with" an eye-tracker 30 (and vice-versa) means that the eye-tracker 30 tracks the eye corresponding to the eyepiece 24. For example, a "right" eyepiece 24 corresponds to the right eye. The eye-tracker 30 that corresponds to right eyepiece 24 tracks the right eye.

Eye-tracker 30 may be placed in any suitable location where it can track movement of the eye. In FIGS. 1 and 2, eyepiece 24a includes eye-tracker 30. In other embodiments, eyepiece 24b includes eye-tracker 30 or both eyepieces 24a,b include eye-tracker 30. Moreover, an eyepiece 24 may include eye-tracker 30 and path 26 that directs virtual GUI, or one eyepiece 24 may include eye-tracker 30 and the other eyepiece 24 may have path 26 that directs virtual GUI.

In yet other embodiments, one or more parts of eye-tracker 30 are separate from eyepiece 24. For example, the sensors 62 (and optionally illuminators 64) as shown in FIG. 2 could be attached to a ring located between eyepiece 24a and the eye, e.g., above and separated from the top of eyepiece 24a or coupled (perhaps removably so) directly to eyepiece 24a. Such ring may allow one to retrofit existing binocular eyepieces 22 with an eye-tracker 24 or replace one eye-tracker 24 with another eye-tracker 24. In some embodiments, such ring may allow one to insert eye-tracker 24 into path 26 when eye-tracking is desired, and remove eye-tracker 24 from path 26 when it is not.

Eye-tracker 30 has one or more sensors 62 that detects light reflection from the eye, e.g., from the cornea (e.g., anterior surface), pupil center, limbus, lens (posterior surface), and/or other part of the eye. Sensors 62 generate image data describing the light and sends the image data to computer 20. Sensor 62 may be placed in any suitable location where it can track movement of the eye. In FIG. 1, the reflection from the eye travels along path 26a, and beamsplitter 31 and lens 60 direct the reflection to sensor 62. In FIG. 2, sensors 62 located along the edge of eyepiece 24a proximate to the eye detect the reflection from the eye. Any suitable sensor 62 may be used, e.g., video camera or a charge-coupled device (CCD), complementary metal-oxide-semiconductor (CMOS), or profile sensor. A profile sensor operates by summarizing the values of all pixels in a row and/or a column into a single value. Any suitable sampling rate may be used, for example, a rate in the range of 30 to 50, 50 to 200, 200 to 500, 500 to 1000, or over 1000 Hz.

In certain embodiments, eye-tracker 30 has one or more illuminators 64 that illuminate the tracked eye with light to create reflections that can be sensed by sensor 62. Illuminator 64 may illuminate with any suitable light, e.g., visible or infrared light. Any suitable illuminator may be used, e.g., LED illuminator, halogen lamp, or other suitable illuminator. In other embodiments, light from device or ambient light may be sufficient to illuminate the eye, such that illuminators 64 are not used.

Eye-tracking program 52 of computer 20 interprets a movement of the tracked eye relative to the virtual GUI as an interaction with a selected graphical element, and device control program 54 initiates the command corresponding to the selected graphical element. Eye-tracking program 52 includes known algorithms to determine a gaze direction of the eye from the image data from sensor 62. Processors 42 perform calculations based on the algorithms to determine the gaze direction. Additionally, eye-tracking programs can detect other movement of the eye, e.g., a blink. Given the gaze direction and position of the virtual GUI, processors 42 determine if the gaze has interacted with an element of a GUI in a manner that indicates selection of the element. If an element is selected, device control program 54 initiates the command corresponding to the selected element.

Optics may be used to direct light to eye and to sensor 62. For example, in FIGS. 1 and 2, beam-splitter 31 receives the virtual GUI, receives an image of an object captured by device 32, and directs the virtual GUI and the image along the optical path towards the corresponding eye. As another example, in FIG. 1, beam-splitter 31 receives light reflected from an eye and directs the light towards sensor 62 of eye-tracker 30.

Binocular system 10 allows a user to enter commands with eye movements to any suitable device 32, such as a medical device. Examples of medical devices include ophthalmic surgical, treatment, or diagnostic devices. Mount 34 may be used to connect binocular eyepiece 22 to device 32. Mount 34 may have any suitable size and shape that allows connection of binocular eyepiece 22 to device 32.

Figure 3A:
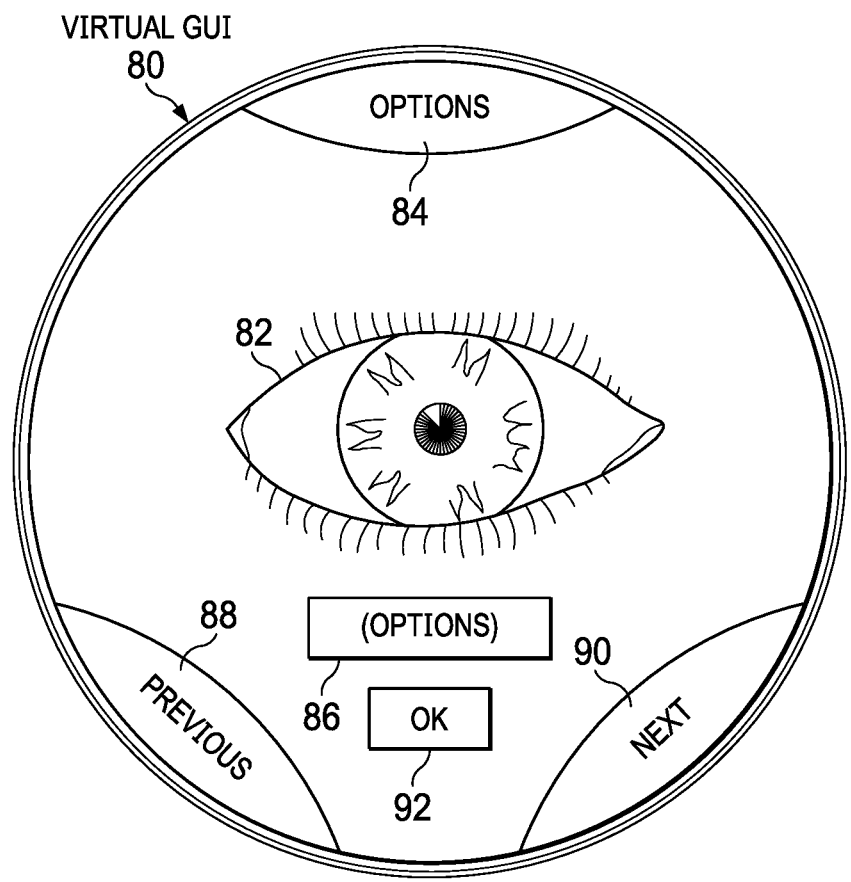
FIG. 3A illustrates an example of a virtual GUI.
Figure 3B:
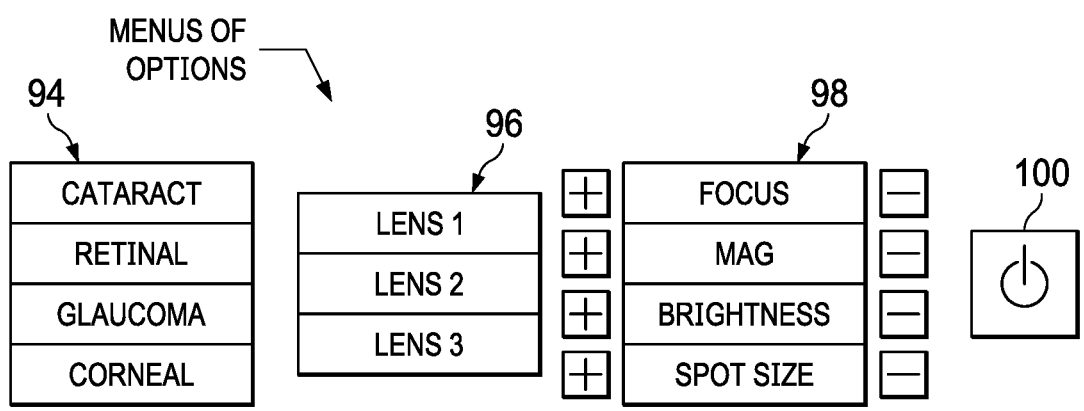
FIG. 3B illustrates examples of menus of options that can be displayed in the virtual GUI of FIG. 3A.

FIG. 3A illustrates an example of a virtual GUI 80, and FIG. 3B illustrates examples of menus of options that can be displayed in virtual GUI 80. In the illustrated example, virtual GUI 80 is overlaid onto an image of an object 82 being viewed through binocular eyepiece 22. Virtual GUI 80 includes graphical elements that can be selected via eye gaze including an options element 84, an options display area 86, a previous element 88, a next element 90, and an OK element 92. Options element 84 corresponds to a command to display one or more menus of options. Menus list options that a user can select via eye gaze. Example menus include a procedures element 94, a lens element 96, a microscope element 98, and an on/off element 100. Procedures element 94 lists surgical procedures that can be selected, and lens element 96 lists types of lenses that can be selected. Microscope element 98 lists features of a microscope that can be adjusted by selecting a PLUS element corresponding to a command to increase the feature or a MINUS element corresponding to a command to decrease the feature. On/off element 100 can be selected to turn the virtual GUI on or off.

Previous element 88 corresponds to a command to move backwards, e.g., move to the previous menu, to the previous option on the list of a menu, or to a previous step in the surgical procedure. Next element 90 corresponds to a command to move forwards, e.g., move to the next menu or to the next option on the list of a menu. OK element 92 corresponds to a command to accept. For example, user may select an option from a menu, and virtual GUI 80 may display a question asking the user to confirm the selected option. The user may select OK element 92 to confirm. Of course, virtual GUI 80 may have any suitable graphical elements (of any suitable size or shape) that can perform any suitable commands.

Figure 4:
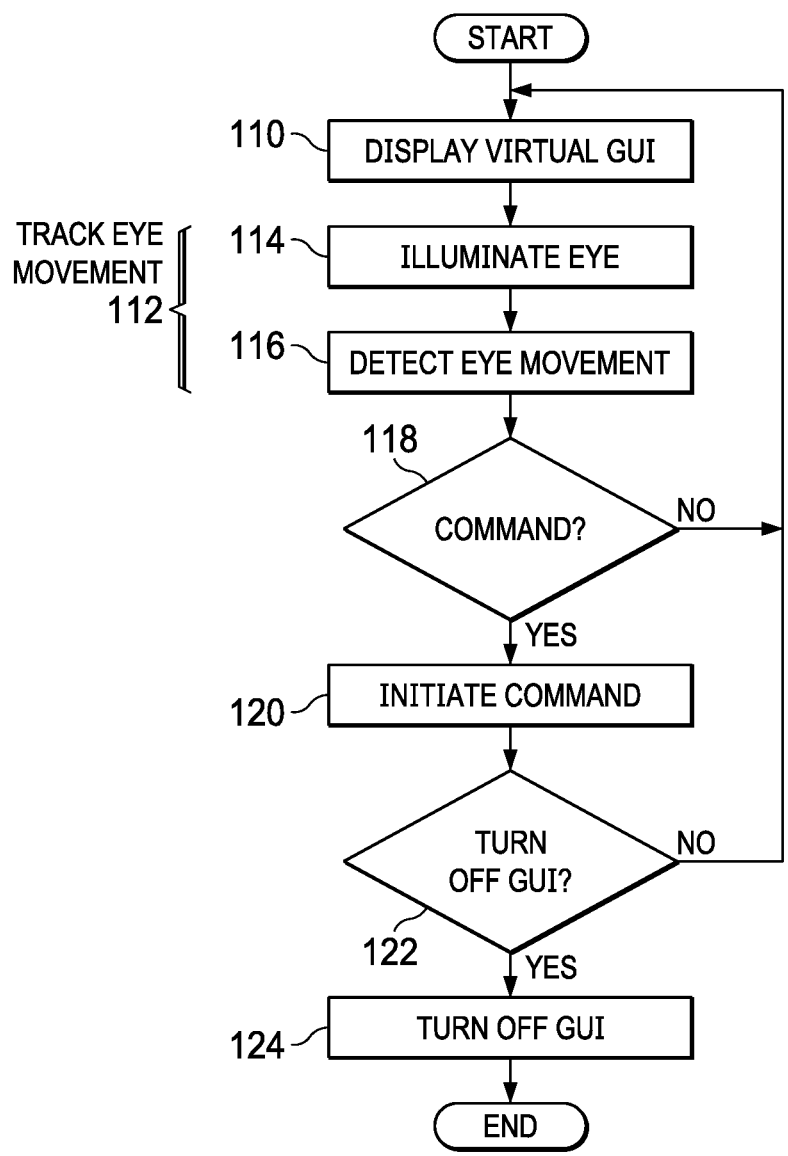
FIG. 4 illustrates an example of a method of entering commands with eye movements that may be used with the systems of FIGS. 1 and 2.

FIG. 4 illustrates an example of a method of entering commands with eye movements that may be used with system 10 of FIGS. 1 and 2. The method starts at step 110, where binocular eyepiece 22 displays a virtual GUI that may be viewed by at least one eye of a user. Eye movement of an eye of the user is tracked at step 112 via steps 114 and 116. Illuminators 64 illuminate the eye at step 114. Sensor 62 detects movement of the eye at step 116 by detecting light reflected from the eye. Sensors 62 generate image data describing the light and sends the image data to computer 20.

Computer 20 determines whether the user has selected a command at step 118. Computer 20 determines whether an eye movement relative to the virtual GUI corresponds to selecting a graphical element of the GUI, indicating the user has selected the command corresponding to the element. If a command has not been selected, the method returns to step 112 to continue to track movement of the eye. If a command has been selected, the method proceeds to step 120 to initiate the selected command. The method checks at step 122 if the user has entered a command to turn off the virtual GUI. If there is no command to turn off the GUI, the method returns to step 112 to continue to track movement of the eye. If there is a command, the method proceeds to step 124 to turn off the GUI and the method ends.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors (e.g., a chip that resides in computers). Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A binocular system for entering commands, comprising:
   a computer configured to generate a virtual graphical user interface (GUI) comprising one or more graphical elements, each graphical element corresponding to a command; and
   a binocular eyepiece comprising a plurality of eyepieces, each eyepiece having an optical path, each optical path configured to direct an image of an object towards a corresponding eye of a pair of eyes:
      the optical path of at least one eyepiece configured to direct the virtual GUI towards the corresponding eye; and
      at least one eyepiece is associated with an eye-tracker configured to track movement of the corresponding eye relative to the virtual GUI to yield a tracked eye, the eye tracker further comprising abeam-splitter configured to:
   receive the image and direct the image along the optical path towards the corresponding eye; and
   receive light reflected from the corresponding eye and direct the light towards a sensor of the eye-tracker; and
   the computer further configured to:
      interpret a movement of the tracked eye relative to the virtual GUI as an interaction with a selected graphical element; and
      initiate the command corresponding to the selected graphical element.

2. The system of claim 1, wherein the eye-tracker comprises:
   one or more sensors configured to track the movement of the tracked eye.

3. The system of claim 1, wherein the eye-tracker comprises:
   one or more illuminators configured to illuminate the tracked eye; and
   one or more sensors configured to track the movement of the tracked eye.

4. The system of claim 1, wherein the eyepiece with the optical path configured to direct the virtual GUI comprises a beam-splitter configured to:
   receive the virtual GUI;
   receive the image; and direct the virtual GUI and the image along the optical path towards the corresponding eye.

5. The system of claim 1, wherein the eyepiece with the optical path configured to direct the virtual GUI also comprises the eye-tracker.

6. The system of claim 1, wherein the plurality of eyepieces comprise:
a first eyepiece comprising the eyepiece with the optical path configured to direct the virtual GUI; and
a second eyepiece comprising the eye-tracker.

7. The system of claim 1, wherein the optical paths of the plurality of eyepieces are each configured to direct the virtual GUI towards the corresponding eyes.

8. The system of claim 1, wherein the plurality of eyepieces each comprise an eye-tracker.

9. The system of claim 1, wherein the graphical elements comprise at least one of the following:
an OK element corresponding to a command to accept;
a PLUS element corresponding to a command to increase; and
a MINUS element corresponding to a command to decrease.

10. The system of claim 1, wherein the graphical elements comprise at least one of the following:
a previous element corresponding to a command to move forwards; and
a next element corresponding to a command to move backwards.

11. The system of claim 1, wherein the graphical elements comprise an options element corresponding to a command to display one or more menus of options.

12. The system of claim 1, further comprising a mount configured to attach to a medical device.

13. A method for entering commands using a binocular system, comprising:
generating, by a computer, a virtual graphical user interface (GUI) comprising one or more graphical elements, each graphical element corresponding to a command;
directing, by an optical path of each eyepiece of a plurality of eyepieces of a binocular eyepiece, an image of an object towards a corresponding eye of a pair of eyes;
directing, by the optical path of at least one eyepiece, the virtual GUI towards the corresponding eye;
tracking, by an eye-tracker associated with at least one eyepiece, movement of the corresponding eye relative to the virtual GUI to yield a tracked eye;
receiving, by a beam-splitter of the at least one eyepiece comprising the eye-tracker, the image and directing the image along the optical path towards the corresponding eye;
receiving, by the beam-splitter, light reflected from the corresponding eye and directing the light towards a sensor of the eye-tracker;
interpreting a movement of the tracked eye relative to the virtual GUI as an interaction with a selected graphical element; and
initiating the command corresponding to the selected graphical element.

14. The method of claim 13, further comprising:
tracking the movement of the tracked eye with one or more sensors.

15. The method of claim 13, further comprising:
illuminating the tracked eye with one or more illuminators; and
tracking the movement of the tracked eye with one or more sensors.

16. The method of claim 13, further comprising:
receiving the virtual GUI by a beam-splitter of the eyepiece with the optical path configured to direct the virtual GUI;
receiving, by the beam-splitter, the image; and
directing, by the beam-splitter, the virtual GUI and the image along the optical path towards the corresponding eye.

* * * * *